United States Patent [19]
Salvo

[11] Patent Number: 5,194,001
[45] Date of Patent: Mar. 16, 1993

[54] REINFORCED DENTAL BRIDGE

[76] Inventor: Christopher A. Salvo, 656 King St., Port Chester, N.Y. 10573

[21] Appl. No.: 738,963

[22] Filed: Aug. 2, 1991

[51] Int. Cl.[5] .................. A61C 13/12; A61C 13/225; A61C 5/00
[52] U.S. Cl. ..................................... 433/180; 433/215
[58] Field of Search .............. 433/180, 181, 182, 183, 433/215

[56] References Cited

U.S. PATENT DOCUMENTS

| | | | |
|---|---|---|---|
| 1,211,494 | 1/1917 | Shaw . | |
| 3,641,670 | 2/1972 | Karageorge | 32/6 |
| 4,360,342 | 11/1982 | Salvo | 433/172 |
| 4,380,435 | 4/1983 | Raeder et al. | 433/180 |
| 4,431,417 | 2/1984 | Weissman | 433/180 |
| 4,433,960 | 2/1984 | Garito et al. | 433/215 |
| 4,457,714 | 7/1984 | Klein | 433/180 |
| 4,713,005 | 12/1987 | Marshall et al. | 433/180 |
| 4,735,571 | 4/1988 | Salvo | 433/215 |
| 4,764,116 | 8/1988 | Shoher et al. | 433/180 |
| 4,820,157 | 4/1989 | Salvo | 433/180 |
| 4,877,400 | 10/1989 | Holsclaw | 433/183 |
| 4,950,162 | 8/1990 | Korber et al. | 433/180 |

Primary Examiner—Gene Mancene
Assistant Examiner—Nicholas D. Lucchesi
Attorney, Agent, or Firm—Lowe, Price, LeBlanc & Becker

[57] ABSTRACT

A reinforcing frame for a dental bridge is described. The frame consists of a main support bar which is bent so that ends may be mounted in abutment teeth spaced above the central portion where the pontic will be formed. A pair of cross bars are then mounted at the central portion extending equidistantly, perpendicular to the longitudinal axis of the main support bar. The cross bars or rings and ellipses may be attached in a conventional fashion such as by welding or by spot welding. Optionally, U-shaped wires depend from the ends of the cross bars. The dental prothesis is then formed around the cross bars and main support bar so that the occlusal surface thereof is above the main support bar and there is no more than about 1.5 to 2 mm of bulk composite or porcelain extending beyond a reinforcing metal member. An additional support bar can be provided when cross bars are mounted below and/or above the main bar. This bar is mounted below the cross bars extending parallel to the main support bar.

40 Claims, 2 Drawing Sheets

REINFORCED DENTAL BRIDGE

FIELD OF THE INVENTION

This invention relates to the field of dentistry and, in particular, to dental bridges used to permanently replace missing teeth.

BACKGROUND OF THE INVENTION

In the past, installation of dental bridges involved a lengthy process of massive restoration or removal of significant portions of abutment teeth. The tooth portion then had to be capped to be restored. The operation then was accompanied by significant patient discomfort and expense. This invention relates to an improved reinforced dental bridge which may be rapidly mounted without massive removal of abutment teeth and which, by reinforcement, provides a much stronger prosthesis and a much more attractive end result.

DESCRIPTION OF THE PRIOR ART

In my prior U.S. Pat. No. 4,360,342, there is described a procedure for providing a dental bridge without massive restoration or removal of significant portions of abutment teeth. A bar, rod, mesh or other similar support was provided with a pontic retained thereon. The dental preparation then called for removal of from about 0.5 to about 2.5 mm from the abutment teeth down to just below the enamel-dentin junction to receive the support. Pins, screws or the like were also used to secure the support to the abutment teeth.

In my prior U.S. Pat. No. 4,735,571, a novel procedure for splinting mobile teeth was described. In that procedure, a bar having dimensions preferably of about 1 mm by 2 mm in cross-section was used. The bar preferably also had a plurality of spaced holes therein wherein screws or pins could be inserted. The bar also had ribs for reinforcement on an upper surface. The dental preparation used in the mobile tooth and abutment teeth was only to the minimum depth necessary to insert the bar. The bar further was bonded in place with a bonding agent and then covered with an opaque surface. Only minimal removal of enamel to the enamel dentin juncture or slightly beyond was required. In the absence of carries, extensive excavation of tooth structure was not required.

The preferred metal bar to be used was a chrome cobalt alloy although other metals such as titanium could be used.

Accordingly, the disclosures of my prior U.S. Pat. Nos. 4,360,342 and 4,735,571 are hereby incorporated by reference.

Subsequently, there have been other attempts to provide a dental bridge with prefabricated pontic. For example, in U.S. Pat. No. 4,764,116, the prefabricated pontic has an adjustable framework of a plurality of pliable metal web members designed to be bent to fit the space required and then fabricated as an internal skeleton for a porcelain pontic.

In U.S. Pat. No. 4,950,162, there is recognized the need for standardizing a bridge framework for industrial production also. In that patent, however, the bridge designed was complicated. A horizontal support bar was intended to extend between abutment teeth. The bar was formed with a longitudinal groove forming a V the length thereof. In addition, a longitudinally extending reinforcing rib depended from the bar including semicircular ribs extending the length of the edentulous site. It was indicated that further ribs could be provided extending perpendicular to the longitudinal axis of the bar, but also depending therefrom. The framework then was described as adjustable to different size areas by cutting the bar itself to length. There was no provision for modification of the longitudinally extending rib to accommodate the space between abutment teeth.

SUMMARY OF THE INVENTION

It has been discovered, however, that a bridge framework can be provided utilizing a bar similar to that disclosed in my U.S. Pat. No. 4,735,571. The bridge framework and, in fact, the entire bridge can be constructed rapidly in the dentist's office.

Initially, only a class 1 dental preparation is provided in the abutment teeth to remove the marginal ridge adjacent to the edentulous site. The bar could be a non-metal such as a porcelain, polymer, a plastic or a composite, each of which may contain reinforcing fibrils. These may be of nylon or variations of non-metallic fibrils of glass or different elements including strontium, barium and boron fibrous whiskers. These polymeric reinforcements may be longitudinally and/or amorphically oriented along the long axis of the bridge. The bar could also be a metal such as titanium or a chrome cobalt alloy and may have a plurality of holes therein. The bar is first cut to length and bent so that while the ends rest in the abutment teeth, the center portion whereon the pontic or pontics will be mounted is spaced below what would be the occlusal surface. The polymeric bridge may be hand formed. Other means may also be used such as CAD/CAM procedures using digitized photographs of the dental preparations and prosthesis projected by a focused array of laser beams into a polymeric bath. This forces molecular linkage of polymer in the form of the finished bridge.

At least one second section of the bar is then provided as a cross brace to be mounted at the center of the pontic to be formed and to extend perpendicular to the longitudinal axis of the support bar. The bars may be channel shaped and can be mounted preferably with the channel opening upwardly for the main support bar. The upwardly extending web members of the channel are then notched "Lincoln log" style to receive, in a precise fit, the cross bar. The resultant combination is then welded, preferably, or joined by any other conventional technique. Finally, a U-shaped wire may be attached at either end of the cross bar to depend therefrom. The pontic then can be built up with layers of composite in the conventional fashion to form the bridge. The overall bridge then is mounted in the patient's mouth in the conventional fashion with bonding or cementing.

The bridge framework of this invention will fit any space between abutment teeth merely by cutting the main supporting bar to length. While this does require that the dentist or technician fabricate the bridge framework, as will be obvious to those skilled in the art, the procedures required are not difficult. The framework then functions to provide a metal support which has only, in the ideal finished product, 1.5 to 2 mm of bulk composite resin or porcelain extending away from the metal or physical dental support structure.

In another embodiment of this invention, after the desired number of crossbars are welded or bonded to the main support bar, this bar may be reinforced by one or more additional longitudinal bars mounted either above or below the main support bar, or both. If the reinforcing bar is mounted above, it would extend across the central portion of the main support bar only. If the reinforcing bar is mounted below, it may extend into a special preparation at one or both ends in abutment teeth. In that way both the reinforcing bar and the main support bar would be mounted in abutment teeth. The reinforcing bars may be of any material, either the same as the crossbar and/or the main support bar or different. For example, if the main support bar is titanium, it may be feasible to use one or more reinforcing bars for additional rigidity.

If the bridge of this invention is used to replace one or more front teeth, it most preferably would be rotated 90° and fitted in the lingual side with dental preparations being made in that side of abutment teeth. In this case the crossbar would then extend vertically. The ends of the main support bar would be bent as in the above-described fashion and the pontics would be formed around the crossbars and the central portion of the main support bar.

The bridge of this invention provides excellent stability and the load placed thereon is transferred by the main bar to the abutments.

Accordingly, it is an object of this invention to provide a novel dental bridge reinforced with cross members which can be easily and quickly fashioned in the dentist's office.

It is another object of this invention to utilize a channel shaped support bar and a similar shaped cross member to support a pontic of porcelain or composite or other resin or other acceptable pontic material built up thereon wherein the main support bar extends below the occlusal surface of the pontic and the center thereof lies below the ends of the bar which are mounted in dental preparations in the abutment teeth.

It is another object of this invention to provide a reinforced dental bridge which utilizes a channel shaped main supporting bar wherein the bar is bent so that the portion which mounts the pontic extends below the occlusal surface into the edentulous area whereas the ends are mounted in dental abutment teeth preparations that involve removal of the marginal ridge only. Cross bars are mounted on the main bar support perpendicular to the longitudinal axis thereof which cross bar further supports a U-shaped wire depending from ends thereof so that the pontic itself is built up on the cross bar and depending U-shaped wire. The wire, however, is optional.

These and other objects will become readily apparent with reference to the drawings and following description wherein:

DETAILED DESCRIPTION OF THE INVENTION

As indicated above, the invention uses a channel shaped bar as the main support extending between abutment teeth. Preferably the bar is chrome cobalt, but it could be titanium or made of polymer or composite containing longitudinally or amorphically oriented glass, boron or other non-metallic fibril reinforced polymer or composite or other conventional material. Bars are available either with no holes, 10, 20, or 40 holes per inch. Obviously, the longer the span, the more strength needed in the bar and, therefore, the fewer holes. The bar most resistant to bending is the chrome cobalt, but titanium is more adaptable. Chrome cobalt is also preferred because the entire surface is bondable.

There are a variety of bonding agents available commercially. As identified in my U.S. Pat. No. 4,735,571, suitable bonding agents are commercially available from, for example, Kerr Division of Sybron Corporation of Romulus, Mich., trademark Bond Lite. Minnesota Mining and Manufacturing Company of St. Paul, Minn., also markets Scotch Bond and Den-Mat Inc. of Santa Maria, Calif., markets an acceptable bonding agent under the trademark Ultra-Bond. As will be obvious to those skilled in the art, any desired opaque may also be used. A number of such are on the market are commercially available.

Figure 1:
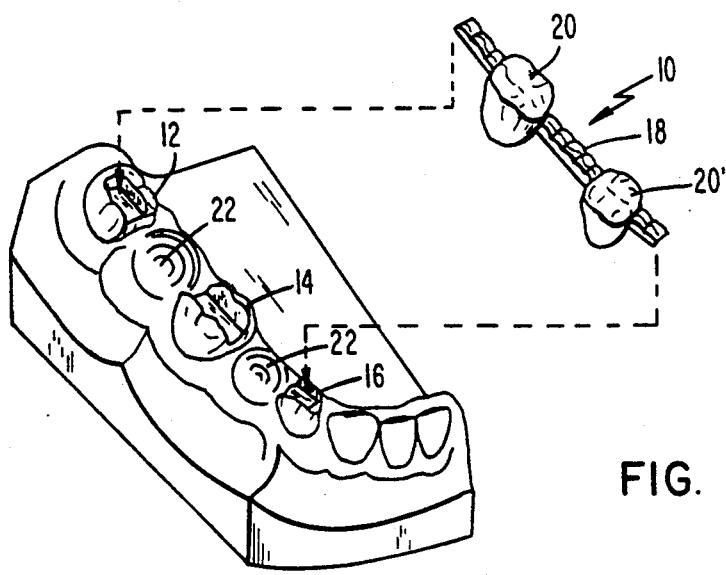
FIG. 1 is an exploded view showing a dental preparation and bridge according to this invention.

To illustrate the invention, attention should be directed to FIG. 1. FIG. 1 is an exploded view of a model utilizing the reinforced bridge of this invention 10. Abutment teeth 12, 14 and 16 have a class 1 dental preparation therein which removes the marginal ridge down to the dentin enamel juncture and in a dimension to receive the bar 18. Bar 18 has mounted thereon two prostheses 20 and 20' which are intended to fit respectively into areas 22 and 22' when the bar 18 rests in the abutment preparations in teeth 12, 14 and 16. The surface of bar 18 is covered with a hybrid composite resin preferably as is the external surface of the prostheses 20 and 20'. The bar 18 would be secured in the abutment teeth with a suitable bonding agent although pins (not shown) could be used if needed.

Figure 4:
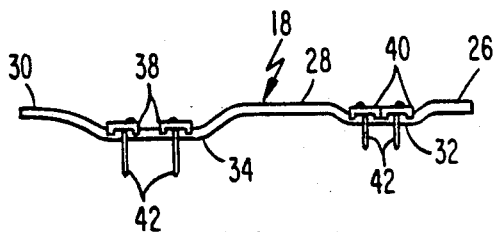
FIG. 4 is a side view of a dental bridge frame according to this invention.
Figure 5:
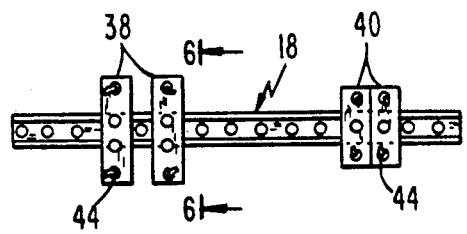
FIG. 5 is a top view of the dental bridge of FIG. 4.

As indicated above, bar 18 is a channel member and may have a plurality of holes 24 drilled therein. The bar is about 1 mm by 2 mm in cross-section and may come in a variety of lengths. In order to form the bridge 10 of this invention, the bar 18 is configured as shown in FIG. 4 so that the portion resting in the abutments 26, 28, and 30 are spaced above the portions 32 and 34 which mount the prostheses 20 and 20'. This is so that the bar can be mounted without a major removal from the abutment teeth and still be disposed substantially below the occlusal surface of the prosthesis teeth 20 and 20'. As shown in FIG. 4, the spacing between, for example, bar portion 32 and 26 exceeds that of, for example, bar portion 34 and 28 due to the different type of teeth involved. This bending will be done by the dentist to custom fit the bridge being prepared to the patient's mouth. Obviously, the bar 18 will be cut to length.

Figure 6:
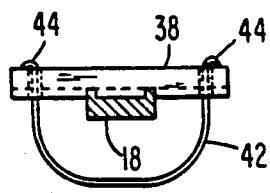
FIG. 6 is a cross sectional view taken along lines 6—6 of FIG. 5.
Figure 7:
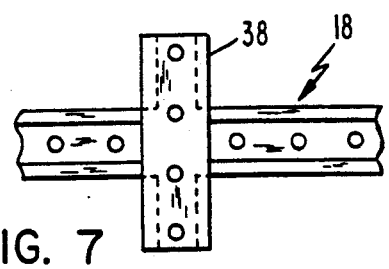
FIG. 7 is a fragmentary view illustrating the inverted cross bar mounted on the main bar.
Figure 8:
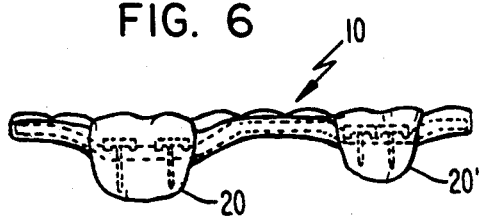
FIG. 8 is a side view of the dental bridge of FIG. 1 showing the supports in phantom.

Cross members 38 and 40 are then mounted on the bar 18. With attention to FIGS. 6 and 7, in the preferred embodiment, the cross bars 38 and 40 are mounted on the bar 18 by "Lincoln log" type notching. The notching may be done by a separating disk or green stone or diamond burr to remove the web members from the channel. The web members are the upstanding sides of bar 18 and the depending sides of cross bar 38. Preferably, the notch will be machined for a close and interlocking fit. The main support bar and cross bars may be manufactured in pre-notched and un-notched forms as well. The cross bars may be also manufactured as notched and un-notched rings and ellipses of different diameters which may be placed around the main support bar where they are attached. These continuous rings and ellipses contain and reinforce composite polymer and procelain pontic build-up. The cross bars 38 and 40 then can be spot welded to the main support bar 18. If a welder is not available, the notched surfaces should be cleaned and then coated with unfilled resin. The cured bonding agent is then covered over with a desired shade of hybrid or macro filled composite. This filled composite covering will secure the cross bars in the desired position for complete pontic build up. The pontic is then built up in the conventional fashion and when complete, the absence of a weld is almost of no consequence.

Figure 9:
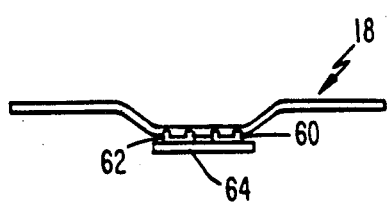
FIG. 9 is a side view similar to FIG. 4 showing an alternate embodiment frame of this invention.

With attention to FIG. 9, the cross members can be mounted below the main support bar 18 via the preferred method of spot-welding. As shown in this embodiment, cross members 60 and 62 are notched rather than the main support bar 18. Furthermore, an additional support bar 64 may be added on the lower surfaces of the cross members. Bar 64 then would have a longitudinal axis contained in the same plane as that of support member 18.

Figure 10:
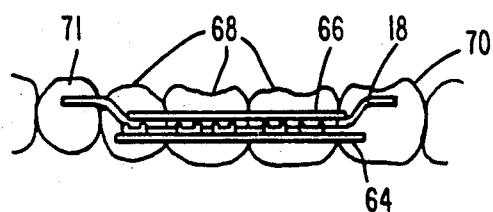
FIG. 10 is a side view illustrating the replacement of three teeth and reinforcement of the main support bar.

With attention to FIG. 10, if additional occlusal stress resistance is needed, a second bar 66 may be utilized either alone or in combination with a lower bar 64 on main support bar 18. Such additional support could be necessary when a plurality of pontics 68 are to be mounted on abutment teeth 70 and 71.

Figure 11A:
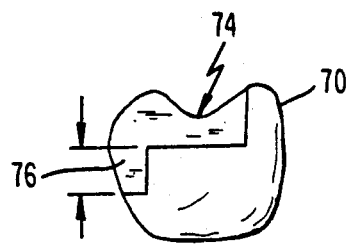
FIG. 11A is a side view of an abutment tooth having a dental preparation for receiving a bridge similar to FIG. 10.
Figure 11B:
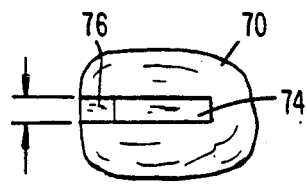
FIG. 11B is a top view of the tooth of the dental preparation of FIG. 11A.

It will be noted that the right side of lower bar 64 may extend into the abutment tooth 70. With attention to FIGS. 11A and B, in addition to the preparation 74, a lower preparation 76 is provided to receive the end of the lower bar 64. In this way additional support in the abutment tooth can be provided for the bridge. Both the end of main support bar 18 and lower reinforcing bar 64 are mounted in the dental preparation in the usual fashion. As also shown in FIG. 10 it may be desirable to anchor only one end of reinforcing bar 64 in an abutment tooth, or as will be obvious to those skilled in the art, the bar can be extended into tooth 71 and a dental preparation provided therefor similar to that shown in FIGS. 11A and 11B.

These cross bars 64 and 66 may be made of metal and welded or attached to cross members 60 and 62 in any conventional fashion, or it may be of a non-metal such as porcelain, glass, boron or other fibers, or resins such as "Kelvar" by DuPont.

Additionally, the bridge and bars may be made of polymer or composite containing longitudinally and/or amorphically oriented glass and or boron whisker fibers including block glass inserts.

Figure 3:
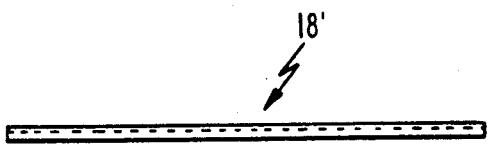
FIG. 3 is a side view of said bar with the holes deleted for clarity.

U-shaped wire members 42 are then mounted in holes respectively at the ends of cross bars 38 and 40, preferably, by bending the ends 44 over as shown, for example, in FIGS. 3 and 4. The wires 42 are optional, but preferred.

Figure 2:
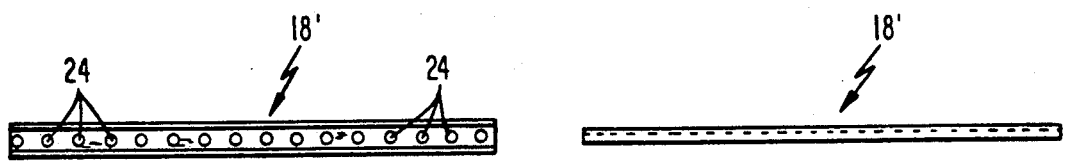
FIG. 2 is a top plan view of the main supporting bar.
Figure 12:
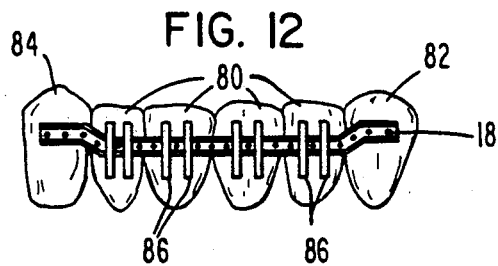
FIG. 12 is a view similar to FIG. 10 illustrating the replacement of four front teeth with the bridge of this invention.

With attention to FIG. 12, the bridge of this invention can also be adapted to replace front teeth. FIG. 12 illustrates a bridge replacing the four lower front teeth 80 with a bridge anchored to abutment teeth 82 and 84. The bridge consists of a main support bar 18 and a plurality of crossbars 86. In this embodiment, two crossbars are shown per pontic 80. As can be seen in FIG. 12, the bridge framework is rotated 90° and mounted in the lingual surface of the abutment teeth 82 and 84. A dental preparation similar to that described above is provided and the crossbars then 86 extend vertically rather than horizontally as shown for example in the framework of FIGS. 2 and 3.

The pontic core bodies are then built on the opaque structure preferably using macrofill and hybrid composite resins in the conventional fashion and then covered over with a micro fill composite. Porcelain may also be used, but titanium cannot be used with porcelain. Light cured or oven cured composite may be used as desired, or a combination. A sandwiching technique is used wherein a hybrid composite resin forms the core with external areas being built up using a macrofilled or hybrid composite. Microfill provides the smoothest and most highly polished finished surfaces where the pontic makes contact with the gingival tissues and is applied externally.

The composite placed under the bar is to be a dual cure, since light cannot penetrate bar metal. Excess over the bar and tooth is removed and light cure is applied. The top of the bar is covered with macrofill or hybrid composite and externally a microfill is used for best polishing characteristics.

Once the pontics and inlay sections of the prosthesis have been polished, the inlay abutment internal surfaces are acid etched, flushed, sterilized with a chlorhexidine gluconate sodium bicarbonate and hydrogen peroxide or other solution and neutralized of any residual acid ions. The internal surfaces then in the conventional fashion are covered with an application of an oxalate dentin bonding agent and then an unfilled resin which may be light or chemically cured. The internal aspect of the inlay sections are covered over with a thin coat of unfilled resin which is then light cured. The prosthesis is then placed into dual cured composite filled abutments. Excess resin is removed from peripheral proximal and occlusal areas. Light curing application is made to all peripheral surfaces for about 60 seconds at each location. The internal surfaces will fully cure by chemical reaction. Upon final polishing, the procedure will be complete.

Pins may be used if necessary. They are placed according to standard procedures through holes in the bar before light curing. Ends typically extend into the channel of the bar and are bent over and opaque. Hybrid composite is placed over the inlay sections and cured. The pontic having been previously completed, the external finish placement of microfill composite is then made, cured, shaped and polished.

As will be obvious to those skilled in the art, the greatest cross bar stability lies with the cross member spot welded and mounted above the bar. However, the cross member could be disposed below the bar if desired. As also noted above, the wires are optional but preferred to fully support the dependent portion of the pontic so that no more than about 1.5 to 2 mm is the maximum distance of an edge of the pontic from reinforcing metal or tooth structure in stress bearing areas.

Figure 13A:
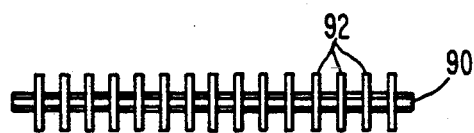
FIGS. 13A and B are top views of alternative embodiments which may be a unitary structure.
Figure 13B:
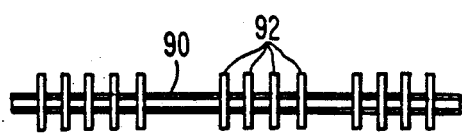

With attention to FIGS. 13A and B, the main support may be marketed as a unitary structure. In this embodiment, the main lateral support 90 would have the cross supports 92 either welded in advance or the structure could be molded and manufactured as a unitary structure. The dentist or technician then would remove the unneeded cross bars 92. As shown in FIG. 13A, the cross supports 92 could be mutually spaced at even intervals along the length of the main support 90, or as shown in FIG. 13B, they may be grouped. In supports for smaller teeth, the cross bars could be about 3 to 4 mm apart and extend laterally away from the cross support 90 about 3 mm. This would be for bicuspids and smaller teeth. In the case of larger teeth, the bars 92 may extend 4 to 5 mm laterally away from the main support 90.

In addition, a wax or plastic model could be marketed to dentists or technicians which would permit the dentist or technician to cast via the lost wax process the support using any metal desired. The unneeded cross supports 92 then could be removed from the wax model before the mold is made.

Further, the cross support bars 92 may be extra long in both molded, manufactured and plastic forms so that they may be bent dependently into a ring, elliptical or circular form to retain pontic mass structure and substance.

In wax or plastic form, the extra long dependently bent support bars may be joined or waxed together to complete the ring (posterior molar and bicuspid pontics) or ellipse (anterior cuspid and incisor pontics) before casting.

In addition, the above procedure was outlined for the purposes of example and not intended to limit application of the bridge of this invention. Any known procedure could be utilized within the scope of this invention.

The invention may be embodied in other specified forms without departing from the spirit or essential characteristics thereto. The present embodiments are therefore to be considered in all respects as illustrative and not restrictive, the scope of the invention being indicated by the appended claims rather than by the foregoing description, and all changes which may come within the meaning and range of equivalency of the claims are therefore intended to be embraced therein.

I claim:

1. A reinforcing frame for a dental bridge comprising:
   a channel-shaped main support bar having sides and a base and end portions for mounting in dental preparations in abutment teeth and at least one central portion for mounting at least one dental prosthesis, the central portion being contained in a first plane and at least one end portion being contained in a second plane the first plane being parallel to and spaced a predetermined distance away from the second plane;
   at least one cross support bar extending perpendicular to the longitudinal axis of said main support bar and mounted across the central portion of said main bar and extending equidistantly from each side thereof, the sides of said main support bar defining a notch with said cross bar being mounted therein, said bars being of the same material and having the same cross-sectional configuration.

2. The frame of claim 1 wherein two cross bars are provided.

3. The frame of claim 1 wherein the main support bar has cross sectional dimensions of about 1 mm by 2 mm.

4. The frame of claim 1 wherein said bars define mutually spaced holes extending the length thereof.

5. The frame of claim 4 further comprising a U-shaped wire reinforcing member depending from said at least one cross bar each end of said wire extending through a hole adjacent a respective end of said at least one cross bar, the ends of said reinforcing member extending through each hole being bent to attach said member and said at least one cross bar.

6. The frame of claim 1 further comprising a U-shaped wire reinforcing member depending from said at least one cross bar each end of said wire member being mounted adjacent a respective end of said at least one cross bar.

7. The frame of claim 1 wherein said at least one cross bar is mounted on said main bar on the lower surface thereof.

8. The frame of claim 1 wherein said at least one cross bar is mounted on said main bar on the upper surface thereof.

9. The frame of claim 1 wherein said bars are a chrome cobalt alloy.

10. The frame of claim 1 wherein said at least one cross bar is mounted on said main support bar by welding.

11. A reinforcing frame for a dental bridge comprising a main support bar having end portions for mounting in dental preparations in abutment teeth and at least one central portion for mounting a dental prosthesis, the central portion being contained in a first plane and at least one end portion being contained in a second plane, the first plane being parallel to and spaced a predetermined distance away from the second plane;
   at least one channel-shaped cross support bar having sides and a base, said at least one cross support bar extending perpendicular to the longitudinal axis of said main support bar and mounted across the central portion of said main bar and extending equidistantly from each side thereof, the sides of said at least one cross bar defining a notch with said main support bar being mounted therein.

12. The reinforcing frame of claim 11 wherein a plurality of cross support bars are provided and mounted on the lower side of said main support bar.

13. The reinforcing frame of claim 12 further comprising an additional support bar having a longitudinal axis contained in the same plane as that containing the longitudinal axis of said main support bar said additional support bar being mounted below said main support bar on the underside of said cross support bars.

14. The reinforcing frame of claim 13 wherein said bars all have the same cross-sectional configuration.

15. The reinforcing frame of claim 14 wherein said bars define mutually spaced holes extending the length thereof.

16. The reinforcing frame of claim 13 further comprising a further additional support having a longitudinal axis contained in the same plane as that containing the longitudinal axis of said main support bar, said further additional support bar being mounted on the upper surface of said main support bar.

17. The reinforcing frame of claim 11 further comprising an additional support bar having a longitudinal axis contained in the same plane as that containing the longitudinal axis of said main support bar, said additional support bar being mounted above said main support bar on the upper surface thereof.

18. The reinforcing frame of claim 11 wherein a plurality of cross support bars are provided and mounted on the upper side of said main support bar.

19. The reinforcing frame of claim 18 further comprising an additional support bar having a longitudinal axis contained in the same plane as that containing the longitudinal axis of said main support bar, said additional support bar being mounted below said main support bar on the under surface thereof.

20. The reinforcing frame of claim 19 further comprising an additional support bar having a longitudinal axis contained in the same plane as that containing the longitudinal axis of said main support bar, said additional support bar being mounted above said cross support bars on the upper surface thereof.

21. Method for reinforcing a dental bridge having a main support bar having end portions intended to be mounted at ends thereof in abutment teeth and at least one central portion intended to mount at least one dental prosthesis comprising the steps of:
bending said bar so that the central portion is contained in a first plane and at least one end portion is contained in a second plane the first plane being parallel to and spaced a predetermined distance away from the second plane;
providing at least one cross support bar extending perpendicular to the longitudinal axis of said main support bar and mounted across the central portion of said main bar and extending equidistantly from each side thereof, the sides of said main support bar defining an interlocking notch with said at least one cross bar being mounted therein, said bars having the same cross-sectional configuration;
whereby the prosthesis can be formed to contain the central portion of the main bar and the at least one cross bar embedded therein.

22. The method of claim 21 wherein two cross bars are provided.

23. The method of claim 22 wherein the cross bars are channel shaped with bases and sides and said bars define mutually spaced holes in the bases extending the length thereof.

24. The method of claim 23 further comprising providing a U-shaped wire reinforcing member depending from said at least one cross bar each end of said wire extending through a hole adjacent a respective end of said at least one cross bar, the ends of said reinforcing member extending through each hole being bent to attach said member and said at least one cross bar.

25. The method of claim 24 wherein the main support bar has cross sectional dimensions of about 1 mm by 2 mm.

26. The method of claim 21 further comprising providing a U-shaped wire reinforcing member depending from said at least one cross bar, each end of said wire member being mounted adjacent a respective end of said at least one cross bar.

27. The method of claim 21 wherein said at least one cross bar is mounted on said main bar on the lower surface thereof.

28. The method of claim 21 wherein said at least one cross bar is mounted on said main bar on the upper surface thereof.

29. The method of claim 21 wherein said bars are constructed of a member selected from the group consisting of a chrome cobalt alloy, titanium and porcelain.

30. The method of claim 21 wherein said at least one cross bar is mounted on said main support bar by welding, or by bonding agents
whereby the prosthesis can be formed to contain the central portion of the main bar and the at least one cross bar embedded therein.

31. Method for reinforcing a dental bridge having a main support bar having end portions intended to be mounted at ends thereof in abutment teeth and at least one central portion intended to mount a dental prosthesis comprising the steps of:
bending said bar so that the central portion is contained in a first plane and at least one end portion is contained in a second plane, the first plane being parallel to and spaced a predetermined distance away from the second plane;
providing at least one cross support bar extending perpendicular to the longitudinal axis of said main support bar and mounted across the central portion of said main bar and extending equidistantly from each side thereof, said at least one cross bar defining a notch having substantially the cross-sectional dimensions of said main support bar, said main support bar being mounted in said notch; whereby the prosthesis can be formed to contain the central portion of the main bar and the cross bar having the main bar mounted therein.

32. The method of claim 31 wherein a plurality of cross bars are provided.

33. The method of claim 32 wherein at least two cross bars are provided said cross bars being mounted below the main support bar said method further comprising providing an additional support bar oriented so that the longitudinal axis thereof is contained in the plane containing the longitudinal axis of the main support bar, said additional support bar being mounted along the undersurface of said cross support bar members.

34. The method of claim 33 further comprising a further additional support bar oriented so that the longitudinal axis thereof is contained in the plane containing the longitudinal axis of the main support bar, said additional support bar being mounted along the under surface of said main support bar.

35. The method of claim 32 wherein at least two cross bars are provided, said bars being mounted above the main support bar, said method further comprising providing an additional support bar oriented so that the longitudinal axis thereof is contained in the plane containing the longitudinal axis of the main support bar, said additional support bar being mounted along the under surface of said main support bar.

36. The method of claim 35 further comprising providing an additional support bar oriented so that the longitudinal axis thereof is contained in the plane containing the longitudinal axis of the main support bar, said additional support bar being mounted along the under surface of said cross support bar members.

37. The method of claim 32 wherein at least two cross bars are provided said cross bars being mounted above the main support bar said method further comprising providing an additional support bar oriented so that the longitudinal axis thereof is contained in the plane containing the longitudinal axis of the main support bar, said additional support bar being mounted along the undersurface of said main support bar.

38. The method of claim 37 further comprising a further additional support bar oriented so that the longitudinal axis thereof is contained in the plane containing the longitudinal axis of the main support bar, said further additional support bar being mounted along the upper surface of said main support bar.

39. The method of claim 32 wherein at least two cross bars are provided, said cross bars being mounted below the main support, said method further comprising providing an additional support bar oriented so that the longitudinal axis thereof is contained in the plane containing the longitudinal axis of the main support bar, said additional support bar being mounted along the upper surface of said main support bar.

40. The method of claim 38 further comprising providing a further additional support bar oriented so that the longitudinal axis thereof is contained in the plane containing the longitudinal axis of the main support bar, said further additional support bar being mounted along the under surface of said cross support bar members.

* * * * *